United States Patent [19]

Sussman

[11] Patent Number: 4,723,556
[45] Date of Patent: Feb. 9, 1988

[54] INTRACRANIAL VENTRICULAR CATHETER ASSEMBLY

[75] Inventor: Marvin L. Sussman, Miami, Fla.

[73] Assignee: Cordis Corporation, Miami, Fla.

[21] Appl. No.: 851,550

[22] Filed: Apr. 14, 1986

[51] Int. Cl.$^4$ .............................................. A61B 5/00
[52] U.S. Cl. ..................................... 128/748; 604/97; 604/102
[58] Field of Search ....................... 128/748, 774, 780; 604/8–10, 97, 102

[56] References Cited

U.S. PATENT DOCUMENTS

| | | | |
|---|---|---|---|
| 550,238 | 11/1895 | Allen | 604/102 X |
| 1,922,084 | 8/1933 | Gerow | 604/102 |
| 2,845,930 | 8/1958 | Brown | 604/96 X |
| 3,669,094 | 6/1972 | Heyer | 128/748 |
| 3,795,246 | 3/1974 | Sturgeon | 604/99 X |
| 3,923,065 | 12/1975 | Nozick et al. | 604/102 |
| 4,003,141 | 1/1977 | Le Roy | 128/748 |
| 4,627,443 | 12/1986 | Chubbuck et al. | 128/748 |
| 4,654,027 | 3/1987 | Dragan et al. | 604/99 |
| 4,655,745 | 4/1987 | Corbett | 604/49 |

Primary Examiner—Dalton L. Truluck
Attorney, Agent, or Firm—Henry W. Collins; Thomas R. Vigil

[57] ABSTRACT

The intracranial ventricular catheter comprises a catheter body having a proximal end and a distal end. A connector is located at the proximal end of the catheter body and an inflatable balloon is mounted at the distal end of the catheter body. A stopcock mechanism is mounted along the catheter body at a position distal to the proximal connector. The catheter body has at least one port in a sidewall thereof at a position just proximal to the inflatable balloon. The catheter body has a first passageway extending from the stopcock mechanism to an interior space of the inflatable balloon. The catheter body also has a second passageway extending from the port to and through the proximal connector, to a pressure sensing device connected to the proximal connector.

3 Claims, 6 Drawing Figures

INTRACRANIAL VENTRICULAR CATHETER ASSEMBLY

BACKGROUND OF THE INVENTION

1. Field of the Invention

The present invention relates to an intracranial ventricular catheter assembly for studying intracranial pressure and compliance and for sampling of cerebrospinal fluid. More particularly, the invention relates to a catheter assembly including a catheter having fluid sampling ports, a balloon at the distal end of the catheter by means of which ventricular volume can be increased and decreased quickly, at will, and a pressure gauge for continuous measurement of intracranial pressure.

2. Description of the Prior Art

Heretofore intracranial ventricular catheter assemblies have been provided for monitoring pressure/volume relationships within the intracranial ventricles and for determination of intracranial pressure.

All such previously proposed catheter assemblies provided for direct fluid addition or withdrawal from the intracranial ventricular system. This type of direct fluid contact has a number of disadvantages. For one thing, direct fluid addition increases the risk of infection. Also, the infusion of a volume of fluid into the ventricles precludes intracranial pressure measurement on an uninterrupted basis. If continuous monitoring is required, then the adjustment in volume must be compensated for via a second access site for withdrawal of added fluid, again increasing the risk of infection or tissue injury. Further, by the direct infusion of fluid, the intracranial pressure may also be caused to rise precipitously, even without a beginning elevated baseline, requiring that the infused fluid be immediately removed. In some instances, immediate removal of the infused fluid is not possible, the fluid having become "trapped" within the ventricular space. Consequently, the intracranial pressure may remain elevated for too long a duration while attempts to bring it down by other means are being undertaken.

The catheter assembly of the present invention overcomes many of these disadvantages by providing (1) safe, reliable means for increasing the intracranial volume with no direct contact of infused fluid and cerebrospinal fluid; (2) means for immediate removal of the infused fluid, if necessary; and (3) means for monitoring intracranial pressure simultaneously during pressure/volume change testing, as will be described in greater detail hereinafter.

SUMMARY OF THE INVENTION

According to the invention there is provided an intracranial ventricular elastomeric catheter assembly comprising a catheter body having a proximal end and a distal end. A connector is located at the proximal end of the catheter body and an inflatable balloon is mounted at the distal end of the catheter body. A stopcock mechanism is mounted along the catheter body at a position distal to the proximal connector. The catheter has a port therein at a position just proximal to the distal inflatable balloon. The catheter body has a first passageway therein extending from the stopcock mechanism to an interior space of the inflatable balloon. The catheter body also has a second passageway therein extending from the proximal connector to the port in the catheter body.

Also according to the invention there is provided a method for monitoring intracranial pressure in a ventricular system in a brain using the catheter assembly described above including the steps of: (a) inserting said catheter assembly into a ventricular system of a brain; (b) inflating said inflatable means; (c) monitoring any change in pressure sensed in said second passageway; (d) deflating said inflatable means; and (e) monitoring any change in pressure sensed in said second passageway.

Further according to the invention there is provided a dual lumen catheter assembly for monitoring intercranial pressure in a ventricular system in a brain and for changing the volume of fluid within the ventricular system and thereby changing the pressure in the ventricular system comprising: a dual lumen elastomeric catheter positionable within the ventricular system for sensing pressure through a first lumen of said catheter; inflatable means at the distal end of said catheter positionable within the ventricular system; means for inflating said inflatable means including a second lumen of said catheter; and means including said first lumen for monitoring the pressure sensed by said sensing means before inflation of said inflation means via a hydrostatic column, after inflation of said inflatable means, and after deflation of said inflation means.

DESCRIPTION OF THE PREFERRED EMBODIMENT

Figure 1:
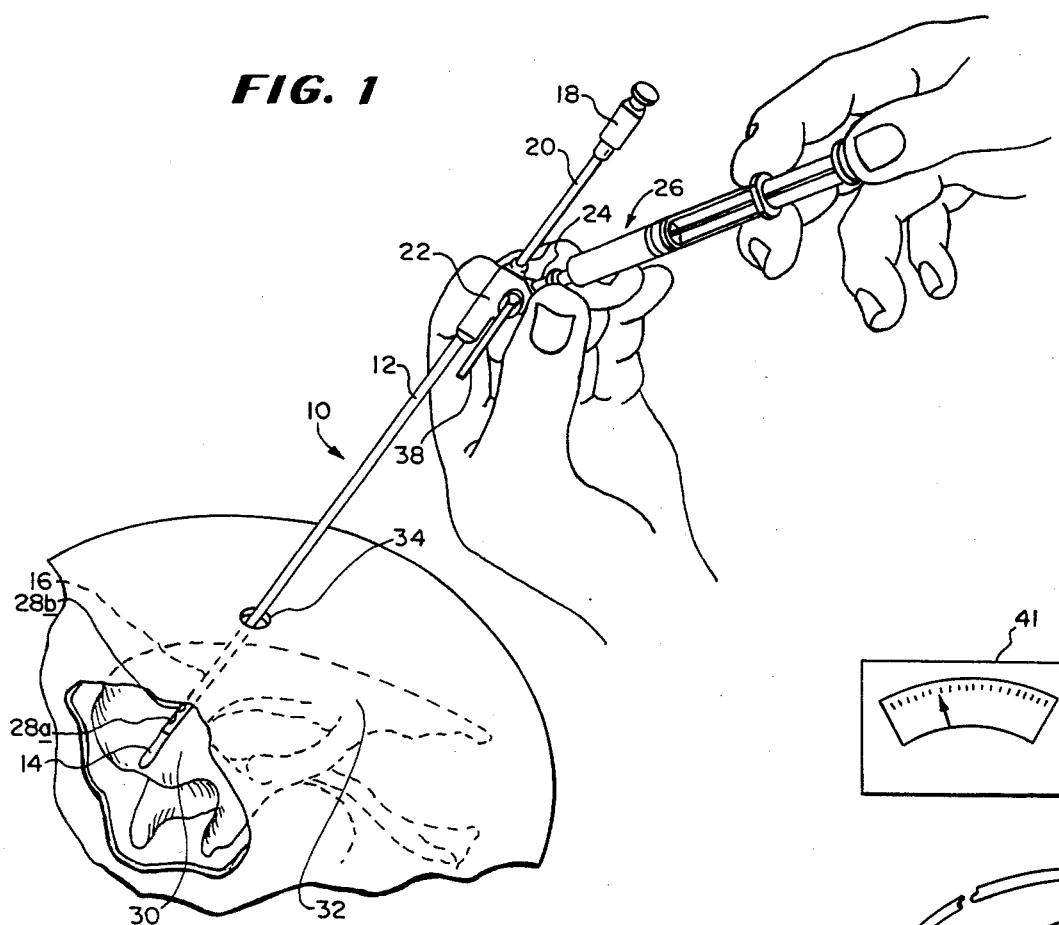
FIG. 1 is a perspective view of the catheter assembly of the present invention and shows the distal end of the catheter of the assembly positioned within the intracranial ventricular system.

Referring now to the drawings in greater detail, there is illustrated in FIG. 1, an intracranial ventricular (ICV) catheter assembly 10 constructed according to the teachings of the present invention.

As illustrated, the ICV catheter assembly 10 comprises a 30 cm long, 7 French (OD) elastomeric catheter body 12 having a balloon 14 attached to a distal end 16 thereof, and a connector 18 attached to a proximal end 20 thereof. The balloon 14 preferably is of such a size as to accept up to 5.0 cc of fluid infusion.

Mounted on the catheter body 12 at a location slightly distal of the proximal connector 18 is a LUER-LOK ™ (bayonet type) stopcock mechanism 22 which is provided with an adapter 24 for receiving a syringe 26 therein. The construction and operation of the stopcock mechanism 22 will be described in greater detail hereinafter.

The catheter body 12 is further provided with at least one port, and preferably two ports, 28a and 28b at the distal end 16 thereof. As shown, the ports 28a and 28b are located just proximal to the location of the attachment of the balloon 14 to the catheter body 12. The catheter body 12 has two passageways (40 and 42 in FIG. 3) which are not shown in FIGS. 1 or 2, being hidden from view, and which are coupled, respectively, to the balloon 14 and the ports 28a and 28b.

Figure 2:
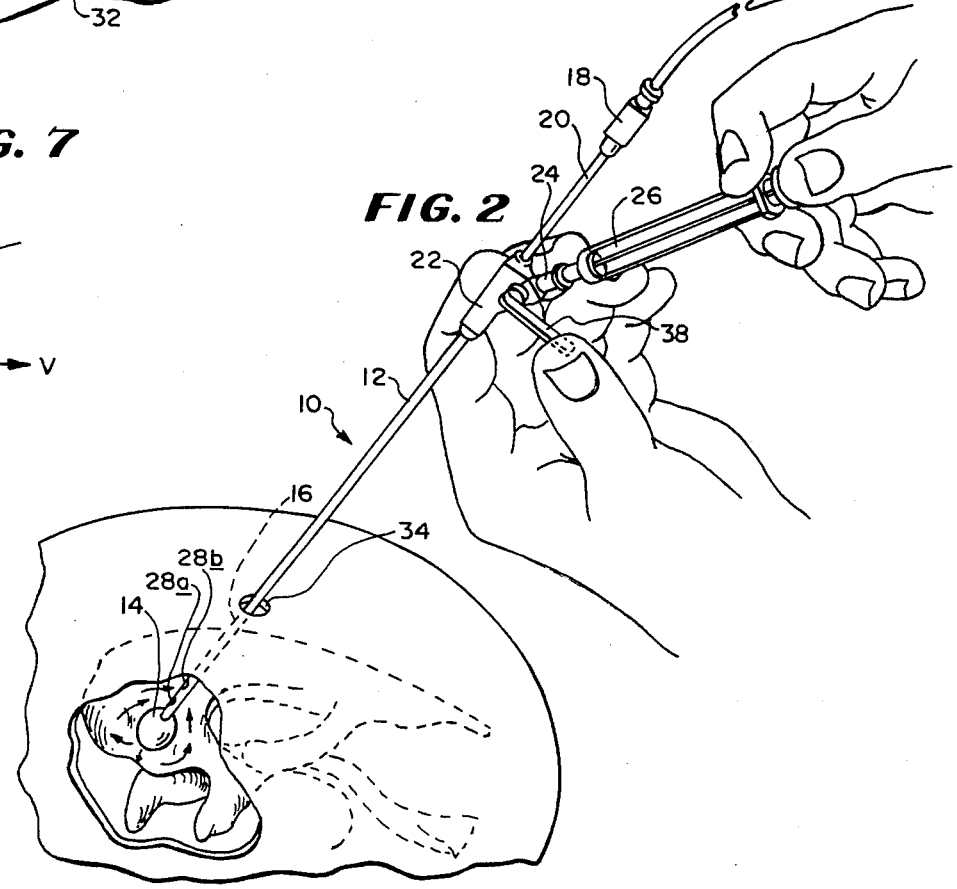
FIG. 2 is a perspective view of the catheter assembly of the present invention similar to the view shown in FIG. 1, and shows the distal end of the catheter within the intracranial ventricular system, an inflatable balloon at the distal end thereof in an expanded state, and a connector at the proximal end of the catheter coupled to a pressure sensing device.

In use, beginning with the illustration in FIG. 1, using an aseptic technique, the distal end 16 of the catheter body 12 is inserted into a ventricular system 30 of a brain 32 via a frontal (for example) twist drill hole 34. Once appropriately positioned within the ventricular system 30, as can be confirmed by conventional skull films, a sterile saline solution, provided within the syringe 26 attached to the catheter assembly 10 via adapter 24 of stopcock mechanism 22, is infused via a first longitudinally extending passageway 40 (FIG. 3) in the catheter body 12, preferably in 0.5 cc dispensation into the balloon 14 at the distal end 16 of the catheter body 12 up to a total infused volume of up to approximately 5.0 cc. Once the volume of saline within the balloon 14 reaches initially 1.5 cc, a lever arm 38 on the stopcock mechanism 22 is rotated to the position illustrated in FIG. 2 to lock the balloon 14 in an inflated condition, as illustrated in FIG. 2. This procedure is repeated in fixed volume increases, at the option of the physician.

Upon inflation of the balloon 14 within the ventricular system 30 a change (increase) in ventricular pressure is produced in response to the increase of up to 5.0 cc in ventricular volume. Since there is an increase in volume, and hence in internal pressure, the cerebrospinal fluid within the ventricular system 30 will tend to move away from the balloon 14 and find an area of least resistance. The ports 28a and 28b formed within the catheter distal end 16 offer such least-resistance escape path for the cerebrospinal fluid in response to the volume/pressure increase brought on by inflation of the balloon 14.

A pressure sensing device 41 such as a pressure transducer, is coupled to the catheter assembly 10 via the proximal connector 18 and is connected via a second longitudinally extending passageway 42 (FIG. 3) in the catheter body 12 to the ports 28a and 28b. As cerebrospinal fluid enters passageway 42 and travels within the passageway 42 toward the pressure sensing device 41, the displacement of fluid within the second passageway 42 (which is prefilled with fluid for hydrostatic column) is measured by the pressure transducer 41 and thus provides means for obtaining a measurement of an increase in intracranial pressure relative to a known increase in intraventricular volume and allows for calculation of relative ventricular compliance, i.e., the pressure/volume relationship, how much increase in fluid volume the ventricular system can handle before the pressure increases.

Further, when the balloon 14 is not being utilized, i.e., inflated, the second passageway 42 in the catheter body 12 may be utilized to continuously monitor intracranial pressure (in the manner of a standard ventricular catheter).

Figure 3:
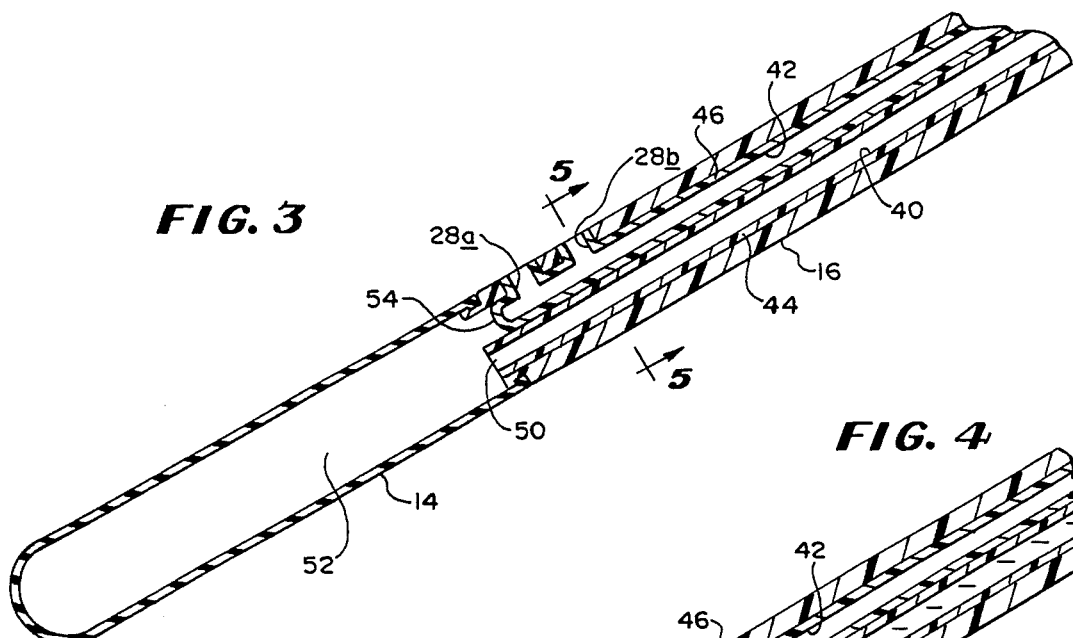
FIG. 3 is a longitudinal sectional view through the distal end of the catheter assembly and shows the balloon of the assembly in a contracted state.
Figure 4:
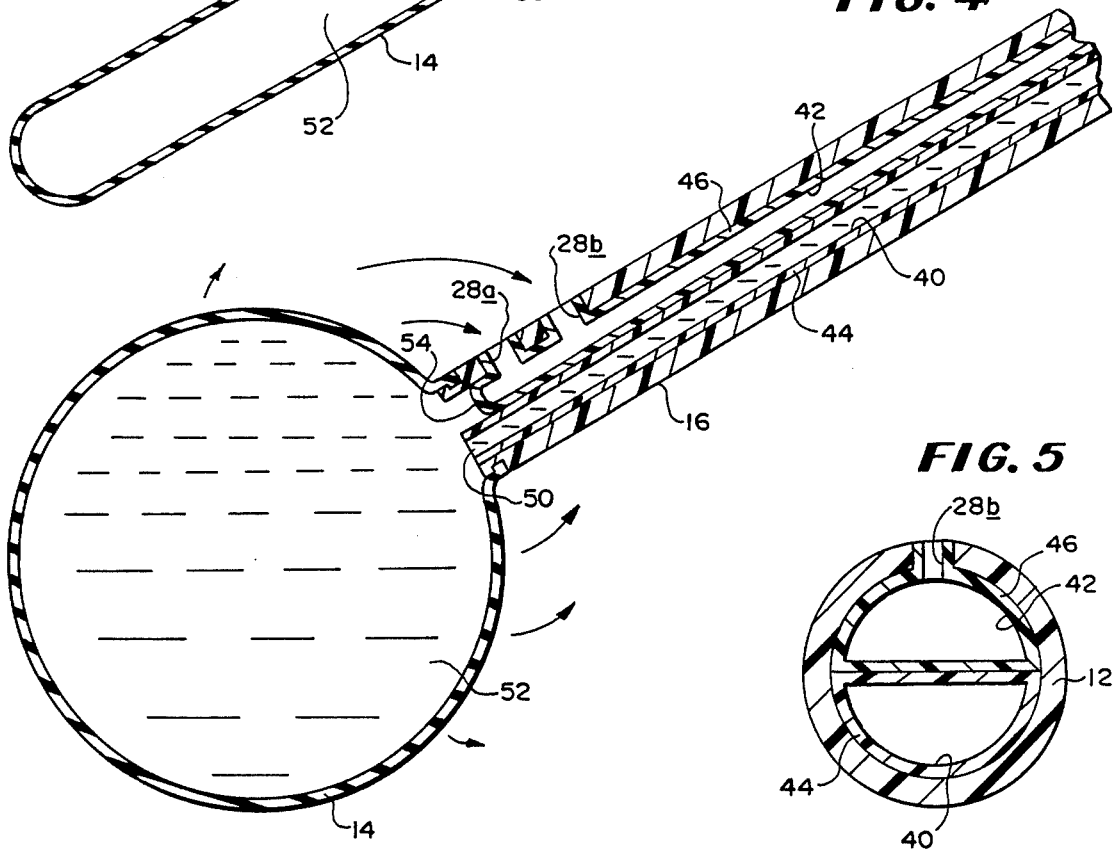
FIG. 4 is a longitudinal sectional view through the distal end of the catheter assembly and shows the balloon of the assembly in an inflated state.

Referring now to FIGS. 3 and 4, there is illustrated therein the internal structure of the catheter body 12 which includes two adjacent tubings 44 and 46 which define the passageways or lumens 40 and 42 therein, respectively. The first tubing 44 extends from a proximal termination (not shown) within the stopcock mechanism 22 where it serves as a continuation of a channel (not shown) extending inwardly from said syringe adapter to a distal opening 50, serving as an input for infusion of the liquid from within the syringe 26 through passageway or lumen 40 into an interior space 52 of the balloon 14.

The lever arm 38 (FIGS. 1 and 2) which is finger manipulatable, is movable from a position where it does not block the channel within the stopcock mechanism 22 (FIG. 1) to a position where it blocks off the channel within the stopcock mechanism 22 (FIG. 2).

The second longitudinally extending tubing 46 extends from its proximal termination (not shown) within proximal connector 18 to a distal end 54. Ports 28a and 28b are located in the side of tubing 46 adjacent to the end 54 and continuous passageway 42 extends between the ports 28a and 28b and the pressure sensing device 32 for monitoring intracranial pressure as described above. The distal end 54 of the second tubing 46 also serves to form a seal or proximal wall for the balloon 14 so that no liquid 36 can escape from within the balloon 14 into the catheter body 12 when the balloon 14 is inflated, as best shown in FIGS. 3 and 4.

Figure 5:
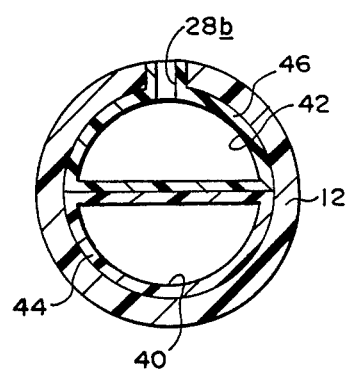
FIG. 5 is a cross-sectional view through the distal end portion of the catheter assembly and is taken along line 5—5 of FIG. 3.

In FIG. 5, is shown the side-to-side positioning of the tubings 44 and 46 within the catheter body 12 and shows the port 28b through the wall of the catheter body 12.

As illustrated the tubings 44 and 46 are both forced to a semicircular configuration in cross section, above. The flat sides of the semicircular tubings 44 and 46 abutt one another along the length thereof and extend together in cross-section across the entire interior space within the catheter body 12. It will be appreciated that this configuration is necessary to provide the proximal closure or seal formed by the distal end 54 of the tubing 46 for the balloon 14 so that the fluid utilized to inflate the balloon 14 is trapped within balloon 14 and cannot leak out and into the ventricular system 30 or back into the catheter body 12.

Figure 6:
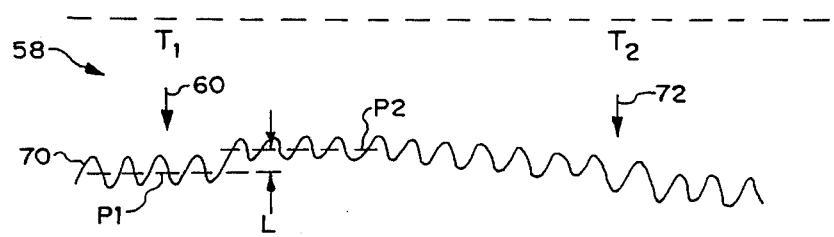
FIG. 6 is a graph of intracranial pressure readings prior to, during, and after inflation of the balloon at the distal end of the catheter assembly of the present invention.

Turning now to FIG. 6, there is shown therein a graph 58 of intracranial pressure versus relative intracranial volume.

In the graph 58, an arrow 60 at the left of the graph 58 designates the point in time T1 at which the balloon 14 is inflated.

As shown, upon inflation of the balloon 14 to increase ventricular volume, the average value P1 of an intracranial pressure baseline waveform 70 shows an increase "L" which is indicative of the compliance of the ventricular system 30. In this respect, if a specific increase in ventricular volume causes a relatively small increase "L" in pressure, the compliance is said to be high, while a great increase in pressure "L" produced with a similar increase in volume indicates a low level of compliance.

Returning to the graph 58, it will be seen that the average value P2 of the baseline waveform 70 is elevated the amount "L" after inflation of balloon 14, providing a specific pressure reading which, when correlated with a known volume change, (an increase in this instance) will allow calculation of relative compliance, compliance being defined as a quality of yielding to pressure or force without disruption, or an expression of the ability to do so.

A second arrow 72 toward the right end of the graph 58 designates a point in time T2 at which balloon 14 is deflated. Upon deflation, and a resulting decrease in volume, it will be seen that the average value of the pressure baseline waveform 70 slowly returns to the previous average value of the baseline waveform 70 which was being generated prior to inflation of balloon 14 at time T1.

Figure 7:
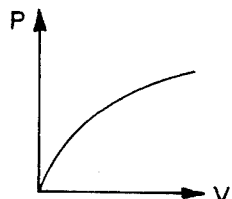
FIG. 7 is a graph of pressure versus volume for normal ventricular compliance.

This graphic illustration of a specific rise in the average value of the pressure baseline waveform 70 relative to a specific, artificially produced rise in ventricular volume, upon a specific amount of inflation of the balloon 14, will provide an accurate measure of pressure/volume parameters, or compliance, which is believed by many to be a more nearly accurate indication of the intracranial status of a subject than the indication provided by the reading of a simple intracranial pressure value. A typical graph of ventricular pressure/volume compliance is shown in FIG. 7.

The catheter assembly 10 of the present invention described above provides a number of advantages. For example, by the provision of the balloon 14, direct contact of cerebrospinal fluid with infused saline is avoided. Further, since the saline is encased within the balloon 14, the infused aliquot may be immediately removed from within the ventricular system 30, if necessary. Also, a continuous reading of intracranial pressure can be obtained during the compliance study procedure, if required.

As an added feature, one could also remove a small amount of cerebrospinal fluid from within the second passageway 42 if a chemical or cytologic examination of the fluid were required, without need of further cranial invasion.

Further, various modifications can be made to the catheter assembly of the present invention without departing from the teachings thereof. For example, the catheter body 12 can be a solid body having the two lumens 40 and 42 formed therein, rather than being hollow and having the two tubings 44 and 46 therein.

Accordingly, the scope of the invention is only to be limited as necessitated by the accompanying claims.

I claim:

1. An intracranial ventricular catheter assembly for determining cranial ventricular pressure, for introducing a sterile isolated fluid into a cranium ventricle and for withdrawing cerebrospinal fluid from a cranium ventricle, said catheter assembly comprising:
   an elongate elastomeric catheter body having a proximal end, a distal end, an outer wall surface, a first passageway extending from a location distal of said proximal end to said distal end of said catheter body and opening onto said distal end, and a second passageway extending from the proximal end of said catheter body to a port at said distal end of said catheter body opening onto said outer wall surface;
   a connector at said proximal end of said catheter body in fluid communication with said second passageway for providing a connection to a pressure transducer or for providing a withdrawal port;
   a stopcock mechanism in fluid communication with said first passageway for allowing or preventing fluid flow of the sterile isolated fluid;
   inflatable means permanently mounted at the distal end of said catheter body and communicating only with said open end of said first passageway for receiving and containing sterile isolated fluid introduced into said first open passageway through said stopcock mechanism; and
   said port being in fluid communication with said second passageway adjacent the distal end of said catheter body and in fluid communication with a cranium ventricle for communicating cranial ventricular pressure to a pressure transducer or for withdrawing cerebrospinal fluid.

2. A method for utilizing an intracranial ventricular catheter assembly comprising a catheter body having a proximal end and a distal end, a connector located at said proximal end of said catheter body, inflatable means mounted at said distal end of said cathether body, a stopcock mechanism mounted along said catheter body at a position distal to said proximal connector, said catheter body having at least one port in the sidewall thereof at a position just proximal to said inflatable means, said catheter body having a first passageway extending from said stopcock mechanism to an interior space of said inflatable means, and said catheter body having a second passageway extending from said port to and through said proximal connector, said method comprising the steps of:
   (a) connecting pressure sensing means to the proximal connector of said catheter assembly;
   (b) connecting a syringe having up to 5.0 cc saline therein to the stopcock mechanism by means of a syringe adapter mounted on said stopcock mechanism;
   (c) forming a drill hole in a skull;
   (d) appropriately positioning through the drill hole and within the ventricular system of the brain the distal end of the catheter assembly;
   (e) reading the intracranial pressure;
   (f) inflating the inflatable means up to 5.0 cc by the addition of 0.5 cc aliquots of saline from the syringe;
   (g) manipulating said stopcock mechanism to lock said inflatable means in an inflated condition;
   (h) monitoring the increase of intracranial pressure produced by inflation of the inflatable means;
   (i) manipulating the stopcock mechanism to unlock the inflatable means from the inflated condition for deflation thereof;
   (j) deflating the inflatable means be drawing the saline back into the syringe;
   (k) monitoring the decrease in the intracranial pressure; and
   (l) continuing to monitor the intracranial pressure.

3. A method for monitoring intracranial pressure in a ventricular system in a brain utilizing a ventricular catheter assembly comprising an elastomeric catheter body having a proximal end and a distal end, a connector located at said proximal end of said catheter body, inflatable means mounted at said distal end of said catheter body, a stopcock mechanism mounted along said catheter body at a position distal to said proximal connector, said catheter body having at least one port in the sidewall thereof at a position just proximal to said inflatable means, said catheter body having a first passageway extending from said stopcock means to an interior space of said inflatable means, and said catheter body having a second passageway therein for the sensing of pressure extending from said portion to and through said proximal connector, said method including the steps of:
 (a) inserting said catheter assembly into a ventricular system of a brain;
 (b) inflating said inflatable means;
 (c) monitoring any change in pressure sensed in said second passageway;
 (d) deflating said inflatable means; and
 (e) monitoring any change in pressure sensed in said second passageway.

* * * * *

UNITED STATES PATENT AND TRADEMARK OFFICE
CERTIFICATE OF CORRECTION

PATENT NO. : 4,723,556

DATED : February 9, 1988

INVENTOR(S) : Marvin L. Sussman

It is certified that error appears in the above-identified patent and that said Letters Patent is hereby corrected as shown below:

Column 1, line 46, after "providing" insert --:--.

Column 6, line 49, "be" should be --by--.

Signed and Sealed this

Twenty-first Day of May, 1991

Attest:

HARRY F. MANBECK, JR.

*Attesting Officer*      *Commissioner of Patents and Trademarks*